(12) United States Patent
Slaga et al.

(10) Patent No.: US 9,011,325 B2
(45) Date of Patent: *Apr. 21, 2015

(54) TISSUE RETRACTOR STAY

(75) Inventors: Allison C. Slaga, Copley, OH (US);
Dawn A. Thompson, Broadview Heights, OH (US)

(73) Assignee: Abeon Medical Corporation, Brecksville, OH (US)

( * ) Notice: Subject to any disclaimer, the term of this patent is extended or adjusted under 35 U.S.C. 154(b) by 486 days.

This patent is subject to a terminal disclaimer.

(21) Appl. No.: 13/307,551

(22) Filed: Nov. 30, 2011

(65) Prior Publication Data

US 2013/0137934 A1    May 30, 2013

(51) Int. Cl.
*A61B 1/32* (2006.01)
*A61B 17/02* (2006.01)

(52) U.S. Cl.
CPC .................................. *A61B 17/0293* (2013.01)

(58) Field of Classification Search
CPC ........................... A61B 17/0293; A61B 17/02
USPC ......................................... 600/227, 217, 206
See application file for complete search history.

(56) References Cited

U.S. PATENT DOCUMENTS

| | | | | |
|---|---|---|---|---|
| 1,708,578 A | * | 4/1929 | Hyde | 600/217 |
| 2,701,562 A | * | 2/1955 | Michael et al. | 600/217 |
| 3,340,974 A | * | 9/1967 | Maucher | 192/70.3 |
| 3,490,455 A | * | 1/1970 | Illig | 600/217 |
| 3,542,015 A | * | 11/1970 | Steinman | 600/217 |
| 3,762,401 A | * | 10/1973 | Tupper | 600/217 |
| 4,274,398 A | | 6/1981 | Scott, Jr. | |
| 4,430,991 A | * | 2/1984 | Darnell | 600/217 |
| 4,434,791 A | | 3/1984 | Darnell | |
| 4,442,150 A | * | 4/1984 | Greiner et al. | 428/53 |
| RE32,021 E | * | 11/1985 | Scott, Jr. | 600/217 |
| 5,174,279 A | * | 12/1992 | Cobo et al. | 600/206 |
| 5,307,790 A | * | 5/1994 | Byrne | 600/206 |
| 5,769,783 A | * | 6/1998 | Fowler | 600/226 |
| 5,785,649 A | * | 7/1998 | Fowler, Jr. | 600/233 |
| 5,899,853 A | | 5/1999 | Fowler, Jr. | |
| 5,938,592 A | * | 8/1999 | Koteles et al. | 600/228 |
| 5,951,467 A | | 9/1999 | Picha et al. | |
| 5,964,697 A | * | 10/1999 | Fowler, Jr. | 600/210 |
| 5,964,698 A | | 10/1999 | Fowler | |
| 6,077,221 A | | 6/2000 | Fowler, Jr. | |
| 6,090,043 A | * | 7/2000 | Austin et al. | 600/217 |
| 6,117,072 A | * | 9/2000 | Fowler, Jr. | 600/217 |
| 6,190,312 B1 | * | 2/2001 | Fowler, Jr. | 600/231 |
| 6,409,731 B1 | * | 6/2002 | Masson et al. | 606/86 R |
| 6,468,207 B1 | * | 10/2002 | Fowler, Jr. | 600/233 |

(Continued)

OTHER PUBLICATIONS

International Search Report for PCT/US2012/067182, dated Feb. 25, 2013.

(Continued)

*Primary Examiner* — Cris L Rodriguez
*Assistant Examiner* — Stuart S Bray
(74) *Attorney, Agent, or Firm* — Pearne & Gordon LLP

(57) ABSTRACT

A surgical stay includes an elastomeric elongated member having a first closed end and a second end and a tissue retention member coupled to the first end thereof. The tissue retention member extends outwardly from the first end of the elongated member. A substantial portion of the length of the elongated member is hollow. The elongated member and the tissue retention member are integrally molded so that no openings are present therebetween.

20 Claims, 7 Drawing Sheets

(56) References Cited

U.S. PATENT DOCUMENTS

| | | | |
|---|---|---|---|
| 6,488,621 B1* | 12/2002 | Rullo et al. | 600/228 |
| 6,561,974 B1* | 5/2003 | Grieshaber et al. | 600/206 |
| 6,689,053 B1* | 2/2004 | Shaw et al. | 600/227 |
| 6,824,511 B1* | 11/2004 | Bell et al. | 600/227 |
| 6,866,940 B1* | 3/2005 | Laughlin | 428/542.2 |
| 7,018,332 B1* | 3/2006 | Masson et al. | 600/227 |
| 7,172,554 B2* | 2/2007 | Gustke et al. | 600/213 |
| 7,887,481 B2* | 2/2011 | Lamadon | 600/230 |
| 8,114,018 B2* | 2/2012 | Park et al. | 600/215 |
| 2003/0055410 A1* | 3/2003 | Evans et al. | 606/1 |
| 2004/0254427 A1 | 12/2004 | Fowler, Jr. | |
| 2005/0119531 A1* | 6/2005 | Sharratt | 600/227 |
| 2007/0156023 A1 | 7/2007 | Frasier et al. | |
| 2007/0161866 A1 | 7/2007 | Fowler, Jr. et al. | |
| 2007/0161867 A1* | 7/2007 | Fowler et al. | 600/233 |
| 2007/0232864 A1* | 10/2007 | Sharp et al. | 600/227 |
| 2007/0235038 A1* | 10/2007 | Alinsod et al. | 128/849 |
| 2007/0238933 A1* | 10/2007 | Alinsod et al. | 600/231 |
| 2008/0269564 A1 | 10/2008 | Gelnett | |
| 2011/0295075 A1* | 12/2011 | Picha et al. | 600/206 |
| 2012/0130180 A1* | 5/2012 | Pell et al. | 600/206 |

OTHER PUBLICATIONS

International Search Report for PCT/US2010-036366 dated Feb. 10, 2011.

\* cited by examiner

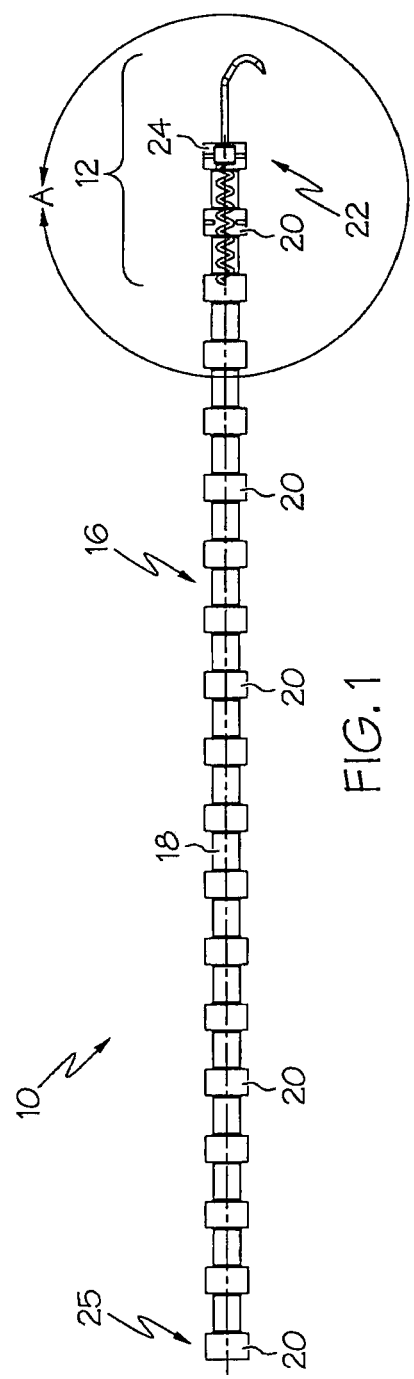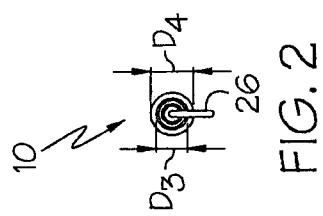

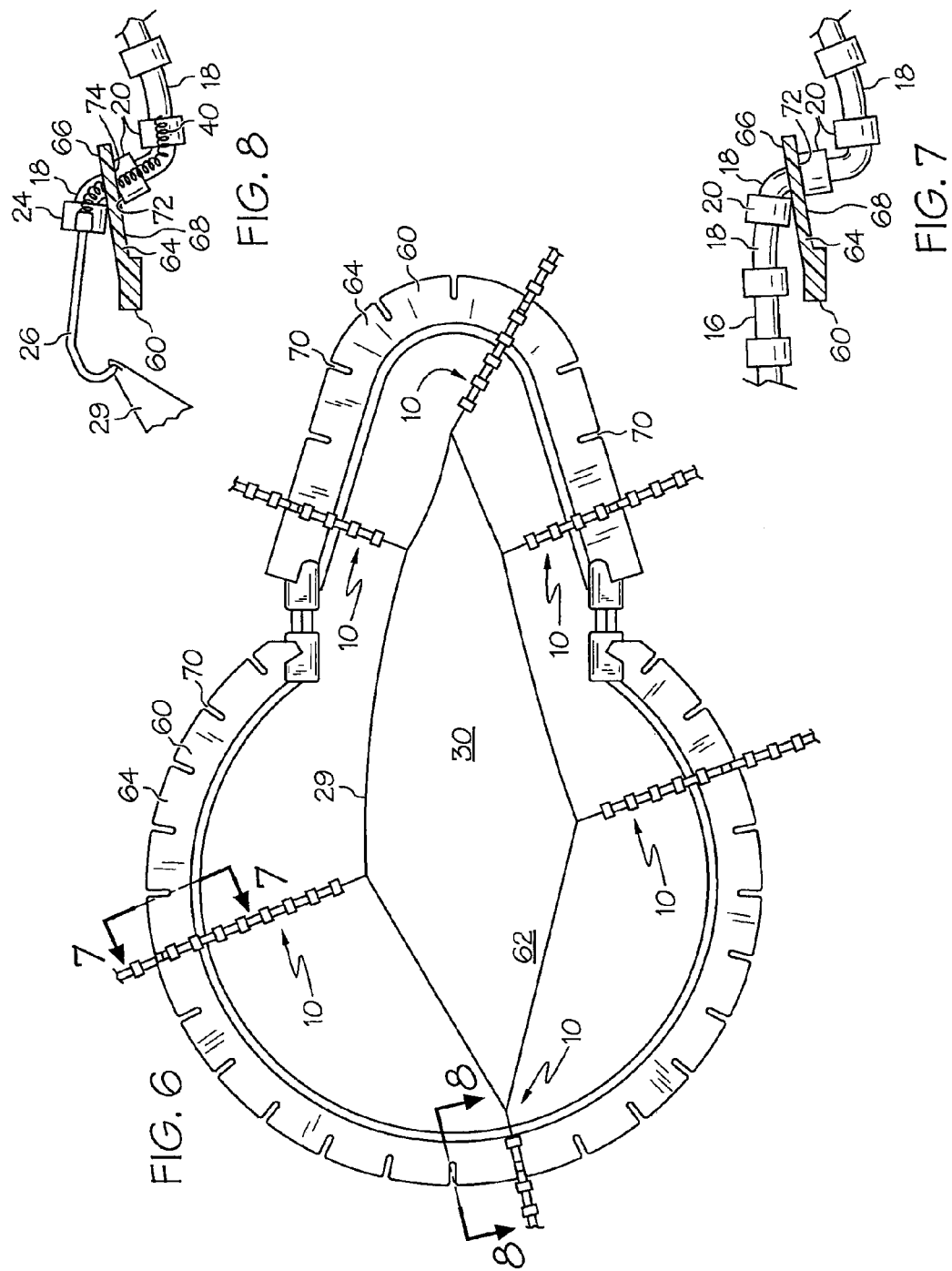

TISSUE RETRACTOR STAY

FIELD

The present invention relates generally to a surgical retractor stay, and more particularly, to a surgical retractor stay having an elongated member.

BACKGROUND

Tissue refraction systems have been developed over the years for use in refracting tissue during surgical procedures to clear the operating field. Such systems may include a retractor frame and a surgical stay. The surgical stay is coupled to the frame in order to retract tissue. Existing surgical stays generally have a retention hook and an elastic elongated member. Such stays have been known to tear due to interaction between the stay and the refractor frame.

SUMMARY

An example surgical stay is shown and described herein.

BRIEF DESCRIPTION OF THE DRAWINGS

FIG. 1 is a side view of an example surgical retention stay;
FIG. 2 is a front view of the surgical stay of FIG. 1;
FIG. 6 is a schematic view of a series of surgical refractor stays in use with an example retractor frame;
FIG. 7 is a sectional view along line 7-7 of FIG. 6;
FIG. 8 is a sectional view along line 8-8 of FIG. 6.

DETAILED DESCRIPTION

Figure 3:
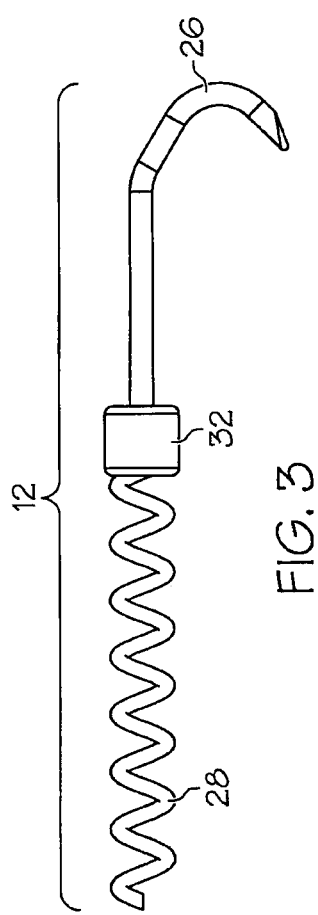
FIG. 3 is a side view of an example tissue retention member for use with the surgical stay of FIG. 1.

Referring to FIG. 1, a surgical retractor stay 10 according to a first example is illustrated. The surgical stay 10 is an elastic handle-less surgical stay. That is, substantially all of the stay 10 can be configured for engagement with a retractor frame 60, and/or surgical instruments, and the stay 10 does not include a handle. Conventionally, a rigid handle region of the traditional surgical stay acts as a lever arm, mechanically amplifying any forces that increase the tissue stress and damage at the distal interface of the stay and the tissue. By contrast, an elastic handle-less stay does not impart the tissue damaging characteristics of a lever arm. Multi-planar elasticity will accommodate retractive forces outside the force vector of refraction without amplifying those forces and further damaging tissue. Tissue damage, especially to sub-dermal and delicate anatomical structures, is reduced, as are pathways of infection and cosmetic blemishes related to tissue damage.

The stay 10 includes a tissue retention member 12, and an elongated elastic member, or elastomeric band 16. Substantially all of the elastomeric band 16 can be configured for engagement with a surgical retractor frame 60 (and/or surgical instruments). For example, the elastomeric band 16 is configured for engagement with a notch 70 of the frame 60 (see FIG. 6), and the stay 10 is inhibited, such as prevented, from moving through the notch 70 (e.g., towards the surgical site 62) by mechanical interference. The band 16 has a longitudinal body 18 with a first end 22. In one example (see FIG. 5A), a plurality of hubs 20 can be disposed around the longitudinal body 18. The first end 22, where the tissue retention member 12 is located, can have one or more hubs disposed adjacent thereto. In one example, as shown, the first end 22 of the band 16 can be defined by at least one hub 24 such that said hub 24 terminates the first end 22 of the band 16. Though identified by a different reference number for clarity, it is understood that hub 24 can be identical to the other hubs 20. A distal end 25 of the band 16 can be located distal to the tissue retention member 12 and can also have one or more hubs 20 disposed adjacent thereto, such as defining and terminating said distal end 25. In another example (see FIG. 5D), the longitudinal body 18 can be relatively smooth without any hubs or the like.

The elastomeric band 16 is made from elastomeric material, such as silicone rubber, urethane polymers, etc. In one example, the band 16 is unitary and formed from a single element or multiple elements, such as a single elastic portion or multiple elastic portions, respectively. The band 16 preferably has a durometer/hardness within a range of about 40 D-60 D, though higher or lower durometer/hardness values are also contemplated. For example, various durometer values can provide various mechanical features, as shown in Table 1:

TABLE 1

| Durometer | Ultimate Elongation | Tensile Modulus (psi) | Tensile Strength (psi) |
|---|---|---|---|
| 40D | 650% | 230 | 1200 |
| 50D | 575% | 310 | 1250 |
| 60D | 450% | 330 | 1520 |

A relatively higher hardness will increase the engagement properties between the hubs 20, 24 and a surgical retractor frame 60. However, this can reduce the elastic qualities of the stay 10. This may not be desirable since a relatively less elastic stay 10 may lose characteristics desired by many surgeons, such as the ability of the tissue retention member 12 to move with the tissue 29 being retained as the surgical site 62 shifts during the operation to minimize tearing of the tissue 29 being retracted. The elastic characteristics also allow the stay 10 to be removed from the tissue 29 and/or the frame 60, and allow the band 16 to conveniently bend as best illustrated in FIGS. 6-8. As illustrated, multiple stays 10 can be used in concert with each other to hold the incision 30 open and thereby provide stable access to the incision 30.

With additional reference to FIGS. 1 and 2, a plurality of hubs 20 are disposed around the body 18 and are spaced apart along the length of the body 18. The hubs 20 extend radially from the body 18. In one example, the entire band 16 is integrally molded in a single molding process, including the hubs 20, 24 and the body 18. The hubs 20, 24 can be integrally molded with the body 18 to form the elastomeric band 16 as a unitary structure, such as a monolithic structure. Preferably, the band 16 is liquid injection molded. Each hub 20, 24 is provided with a frame engagement surface 72 at an end of the hub 20 facing the surgical site 62 for holding contact with the retractor frame 60. Even hub 24 at the first end 22 is provided with a frame engagement surface 72, and is fully functional for engagement with the frame 60. The frame engagement surface 72 can be an annular flat face disposed in a generally perpendicular relationship to the longitudinal axis of the body 18. For example, the band 16 can have an alternating series of cylindrical body portions and larger cylindrical hub 20 portions. The hubs 20, 24 can be provided with a broad, or planar, engagement surface 72 to contact the lower surface 68 of the flange 64 portion of the frame 60 surrounding the notch 70. See FIGS. 6-8. The engagement surface 72 is effective to distribute tension placed on the band away from the body 18 of the band 16 and thus away from the lower surface 68 area immediately adjacent the notch 70.

Still, the hubs 20, 24 can have various other geometries with various other engagement surface structures. For example, the hubs 20, 24 can have any of the geometries discussed in U.S. Pat. No. 6,090,043, the entire disclosure of which is incorporated herein by reference thereto. In various examples, any or all of the hubs 20, 24 can be spherical hubs, conical hubs, semi-spherical hubs, angled or beveled hubs with respect to the longitudinal axis of the band 16 (e.g., to match an angled flange 64 portion of the frame 60), and can have a bowl-shaped or concave engagement surface 72, or even have a molded fillet at an intersection of the body 18 and the engagement surface 72. In addition or alternatively, the body 18 and/or hubs 20, 24 can have various cross-sectional geometries, such as circular, oval, triangular and rectangular. The body 18 can also be relatively smooth without any hubs or the like. The described geometries of the body and hubs are not intended to limit the present invention.

Figure 4A:
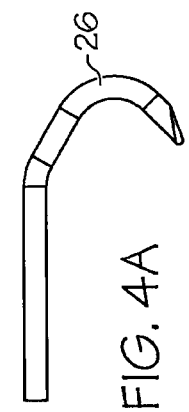
FIG. 4A is a side view of an example tissue-engaging portion of the tissue retention member of FIG. 3.

Turning back to FIGS. 3, 4A and 4B, the tissue retention member 12 generally has a tissue engaging portion 26, extending from the first end 22 of the band 16. The tissue retention member 12 is preferably made from a generally rigid material, such as metal (e.g., stainless steel, aluminum, titanium, etc.) or plastic. The material should be strong enough positively engage tissue 29 of the incision 30 and to withstand the tension forces applied to the surgical stay 10 when engaged with a retractor frame 60. The tissue retention member 12 can be made of a single material, or can be made of multiple materials. For example, the tissue-engaging portion 26 and the anchor portion 28 can be formed from the same or even different materials, depending upon the desired characteristics of the tissue retention member 12. The material is of a surgical grade material, and is preferably autoclavable and reusable, though can also be disposable. In addition or alternatively, the material of tissue retention member 12 can be radiopaque, which is the relative inability of electromagnetism to pass through a particular material, particularly X-rays or similar radiation. The radiopacity of a given tissue retention member can be useful since it can allow the tissue retention member to be tracked before, during, or after a surgical procedure. Alternatively, the tissue retention member can be radiolucent, which is the relatively greater transparency of electromagnetism to pass through the material (e.g., X-rays or similar radiation). The radiolucent property of a given tissue retention member can also be useful since it can allow the tissue retention member to "disappear" and not interfere with a medical scan.

The tissue engaging portion 26 (see FIG. 4A) is configured to grasp tissue 29 surrounding an incision 30 and hold the incision 30 open, and is preferably curved, hook shaped, or otherwise bent, though can also be straight, angular, etc. In various examples, the tissue-engaging portion 26 can be hook-shaped, such as with a 5 mm or 12 mm diameter curved end that can be blunt or sharp, though various other sizes are contemplated. Alternatively, the tissue-engaging portion 26 can be a rake with one or more prongs, a clamp, a multi-prong hook, etc. It is understood that the geometry of the tissue-engaging portion 26 is not intended to limit the present invention.

The tissue retention member 12 further includes an anchor portion 28 (see FIG. 4B) coupled to the tissue-engaging portion 26 at a transition region 32. It is understood that the transition region 32 is depicted schematically in the various Figures (e.g., FIG. 3), and is emphasized for clarity. Various other examples are shown in FIGS. 5A-5D. In practice, the transition region 32 may or may not be an enlarged area, and/or may be formed as a byproduct of the coupling operation used (e.g., a welding operation, soldering, etc.). The anchor portion 28 can be removably or non-removably coupled to the tissue-engaging portion 26 in various manners. In one example, the anchor portion 28 can be non-removably coupled to the tissue-engaging portion 26 by a welding operation. For example, the anchor portion 28 can be spot welded to the tissue-engaging portion 26 to form the tissue retention member 12 prior to coupling with the elastomeric band 16. In other examples, the anchor portion 28 can be coupled to the tissue-engaging portion 26 via soldering, mechanical fasteners, adhesives, friction fits, etc. In yet another example, the anchor portion 28 can be formed together with the tissue-engaging portion 26 as a single, monolithic element. For example, the tissue retention member 12 can be formed (e.g., molded, stamped, rolled, etc.) from a single piece (e.g., single piece of wire, plate, etc.) that is worked to form each of the anchor portion 28 and the tissue-engaging portion 26, or the tissue retention member 12 can even be a single injection molded plastic element, die cast metal, etc.

Figure 5A:
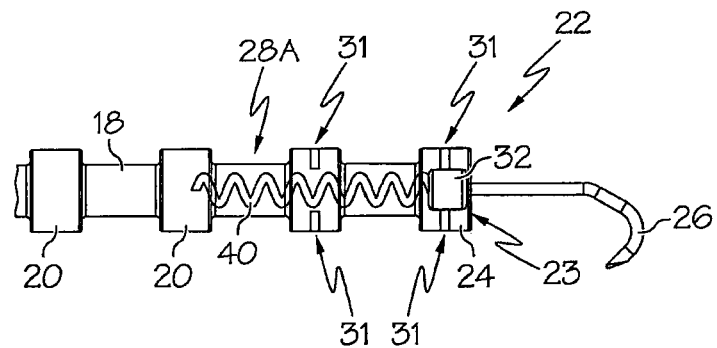
FIGS. 5A-5E are side views of various example tissue retention members embedded in the stay of detail A of FIG. 1.

The tissue retention member 12 can be coupled to the first end 22 of the band 16 such that there is not a detachable connection at the interface thereof. In one example, the anchor portion 28 can be at least partially (such as completely) embedded (such as encapsulated) within the first end 22 of the band 16. It is understood that embedded also includes the anchor portion 28 being received within a recess, hole, etc. that may be either open-ended or closed. The tissue engaging portion 26 may also be partially embedded within the first end 22, or may be completely free thereof. In any case, the tissue engaging portion 26 extends outwardly relative to (such as outwardly from) the first end 22 of the band 16. As described herein, the elastomeric band 16 is formed of a material, such as silicone rubber or urethane polymers, which inhibits disconnection of the anchor portion 28 from the band 16 during use. It is understood that various other materials can also be used to form the band 16. For example, the first end of the elastomeric band 16 can be molded about the anchor portion 28 during the formation of the band 16. As shown in FIG. 5A, one or more mold pin inserts (not shown) can be used during the molding process to maintain proper alignment of the anchor portion 28 within the first end 22 of the band 16, and such inserts can leave behind resultant mold voids 31 that have little bearing on the functionality of the stay 10 and are simply byproducts of the molding process.

The elastomeric band 16 can be formed of a material that closely conforms to the anchor portion 28 to thereby inhibit disconnection during use. For example, during the molded operation the material of the elastomeric band 16 can flow around, into, and/or through the anchor portion 28 to effectively embed the anchor portion 28 within the first end 22 of the band 16. The geometry of the anchor portion 28 can be adjusted to facilitate such close conforming action of the material, such as by providing open areas, hollow portions, apertures, through holes, projections, etc. The anchor portion 28 can extend various distances within the band 16. In one example, the anchor portion 28 can extend a distance equal to about three hubs 20. In another example, the anchor portion 28 can extend a fixed distance, such as about 5/16", 1/2" or more. It can be desirable to make the length of the anchor portion 28 relatively short to thereby reduce material costs and/or facilitate the embedding process.

Figure 5B:
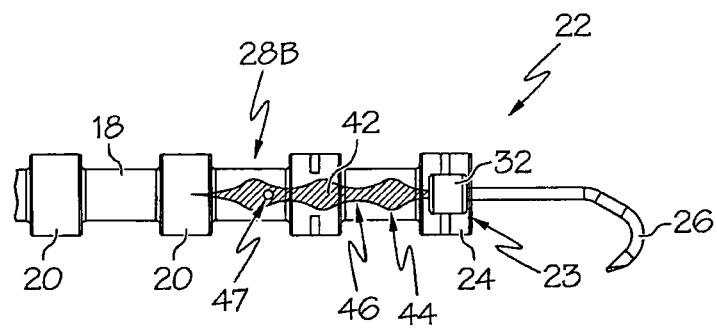
Figure 5C:
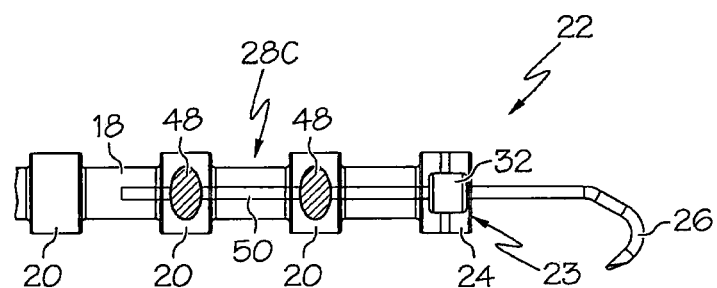
Figure 5D:
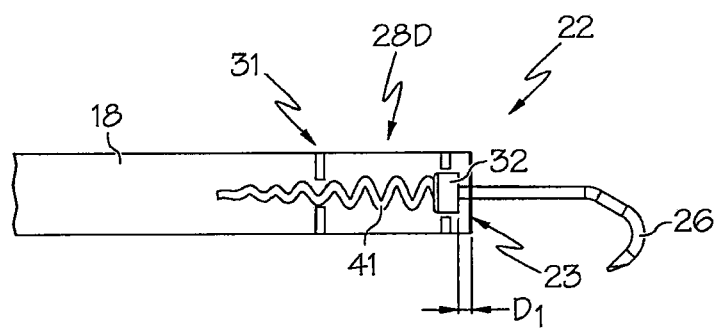

Turning now to FIGS. 5A-5D, which show detail A of FIG. 1, the anchor portion 28 of the tissue retention member 12 can include various geometries. It is understood that the shown examples are merely some of the numerous possible geometries. Various other geometries are contemplated, including combinations of the various discussed anchor portions 28, to inhibit, such as prevent, disconnection (e.g., pullout) of the anchor portion 28 from the band 16 during use. In one example, the anchor portion 28A can include a wire having plurality of bends, such as a coil 40 (see FIG. 5A). The coil 40 can have a generally cylindrical geometry with a generally hollow interior, and can have a generally constant diameter or cross-sectional dimension. For example, the generally hollow interior can permit the material of the band 16 to flow through the coil 40 to provide an increased surface area contact that inhibits disconnection (e.g., pullout) of the anchor portion 28 from the band 16 during use. Additionally, the coil 40 can be bendable about multiple axes. In other examples, the coil 40 can have a variable diameter, cross-sectional dimension, frequency, amplitude, etc. For example, as shown in FIG. 5D, the anchor portion 28D can have a modified coil 41 with an increasing or decreasing cross-sectional dimension that can provide differing amounts of flexibility, pullout strength, or tactile feel along its length. The variations in the modified coil 41 can also provide differing failure modes along its length. The coil 40, 41 can be formed of a spring material, such that the coil 40 exhibits a spring force in various axes. For example, where the coil 40, 41 is embedded in the first end 22 of the band 16, the coil 40, 41 can resiliently seek to obtain a neutral state that extends longitudinally within the elastomeric band 16. Thus, the coil 40, 41 can provide a relatively flexible and bendable feature, and when the first end 22 of the band 16 is curved or flexed (e.g., during a surgery) the coil 40, 41 can provide a resilient opposing force to facilitate holding the tissue 29.

In another example, the anchor portion 28B can include an alternating geometry 42 (see FIG. 5B). That is, the anchor portion 28B can have a geometry that changes between at least two configurations. In one example, the alternating geometry 42 of the anchor portion 28B can be a sinusoidal geometry having a generally repetitive, oscillating geometry with alternating relatively larger portions 44 and relatively smaller portions 46. The alternating relatively larger and smaller portions 44, 46 can enable the anchor portion 28B to provide an increased surface area contact that inhibits disconnection (e.g., pullout) of the anchor portion 28 from the band 16 during use. Though generally repetitive, the amplitude and/or frequency may or may not remain constant. For example, the sinusoidal geometry can include different portions having different repetitive sections. Alternatively, the geometry may not be repetitive. Additionally, the anchor portion 28B can be planar (e.g., flat plate), or twisted (e.g., helical). Further, the alternating geometry 42 may provide a relatively less flexible and bendable feature that can be useful with particular types of tissue-engaging portions 26 or tissue. In one example, the anchor portion 28B can be relatively planar to permit bending along one axis, while resisting bending in the other axes. In addition or alternatively, any of the anchor portions (e.g., 28A, 28B, 28C, etc.) can have a surface morphology or surface treatment that increases or decreases a bonding effect with the bulk material of the band 16. In various examples, the surface morphologies or surface treatments of the anchor portion 28B can include plasma coating, a porous surface, a pillar surface, etc. In another example, the anchor portion 28B can provide one or more open areas 47, such as hollow portions, apertures, through holes, etc. for receiving the bulk material of the band 16 to facilitate retention. In yet another example, the anchor portion 28 can be substantially planar having a generally standard polygonal geometry, such as square, rectangular, circular, elliptical, triangular, etc.

In yet another example, the anchor portion 28C can include a projection 48 (see FIG. 5C). That is, the anchor portion 28C can have one or more projections 48 that may be similar or different. The projection(s) 48 can extend generally outward from a central member 50 of the anchor portion 28C, which can be a central rod or the like, or can even be similar to the other anchor portions 28A or 28B. In one example, the projection(s) 48 can be a bulb, barb, wire element, or the like. The projection(s) 48 can extend outwardly at various angles, such a perpendicular to the central member 50, or at various oblique angles (e.g., an angle oriented towards or away from the first end 22). The projection(s) 48 can be disposed at various locations along the anchor portion 28C. In one example, each of the projections 48 can be arranged on the anchor portion 28 to correspond with a respective hub 20 of the band 16. The projection(s) 48 can enable the anchor portion 28C to provide an increased surface area contact via the hubs 20 that inhibits disconnection (e.g., pullout) of the anchor portion 28 from the band 16 during use. Additionally, the projections 48 can be modified to make the first end 22 relatively more or less flexible and bendable.

Figure 5E:
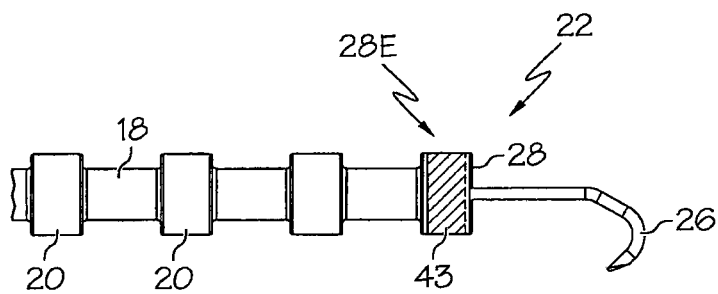

In yet other examples, the anchor portion 28 can be coupled to the first end 22 of the band 16 via mechanical fasteners, adhesives, friction fits, etc. For example, the anchor portion 28 can be glued to the first end 22 of the band 16 and/or retained due to a friction/interference fit with the first end 22. The anchor portion 28 can include surface features, treatments, etc. to facilitate such coupling. In addition or alternatively, the first end 22 can include an aperture, hole, etc. for receiving some or all of the anchor portion 28. The anchor portion 28 may or may not be embedded within the first end 22. In addition or alternatively, the anchor portion 28E can comprise an external coupler 43 (see FIG. 5E), such as a cuff, collar, or the like adapted to be placed over a portion of the first end 22, such as to receive a portion of the first end 22. The tissue engaging portion 26 can be removably or non-removably coupled to the external coupler 43. Similarly, the anchor portion 28 can be configured to be coupled to and retained on the first end 22 of the band 16 by the external coupler 43 including a retaining wire, heat shrink tubing, or the like (not shown) wrapped about the first end 22. The external coupler 43 can also act as the face of the first end 22 for engagement with the surgical frame 60. It is understood that while the external coupler 43 may or may not increase the cross-sectional dimension of the first end 22 of the band 16, substantially all of the elastomeric band (including the external coupler 43) remains configured for engagement with the surgical refractor frame 60 (and/or surgical instruments) such that the stay 10 does not include a handle. It is also understood that while described as external, portions of the external coupler 43 can removably or non-removably extend into or be received by the longitudinal body 18.

In addition or alternatively, any or all of the various anchor portions 28A, 28B, 28C can provide for differing failure modes of the stay 10 about the first end 22. That is, the anchor portion 28 and the material of the body 18 can be configured to avoid unexpected failure modes, such as silicone failure and/or coil failure (e.g., deflection). For example, varying the modulus for each of the anchor portion 28 and bulk material of the band 16 can modify (e.g., enhancing or reducing) the interfacial void formation therebetween. Depending upon the application, the modulus for each of the anchor portion 28 and bulk material of the band 16 may be substantially equal or different in order to create a seamless transfer of force and/or control failure. Generally, if the modulus of the anchor portion 28 is substantially equal to that of the bulk material of the band 16, then both components will react similarly to the overall load applied to the stay 10. However, if the modulus is different between the components, then the components will react differently. It is understood that the modulus can be Young's modulus, shear modulus, bulk modulus, etc.

For example, referring to the coil 40 of FIG. 5A, the coil's maximum deflection distance can be configured to generally coincide with the corresponding durometer's ultimate elongation of the material of the band 16. In addition, maximum force of the coil 40 (e.g., before deflection occurs) can generally coincide with the corresponding tensile strength of the durometer of the material of the band 16. Similarly, the design of the coil 40 can be chosen such that it has a k-value (e.g., spring constant) that is generally equal the modulus of the material of the band 16. These design guidelines can avoid unexpected failure modes. Of course, for other failure modes, the design of the coil 40 can be chosen such that it has a k-value (e.g., spring constant) that is different than the modulus of the material of the band 16.

In one example, the elastomeric band 16 can be formed from a material having a first modulus and the anchor portion 28 can be formed from a generally rigid material having a second modulus. As above, the first modulus can be generally equal to the second modulus to thereby avoid unexpected failure modes. In other examples, the first modulus (band 16) can be greater than the second modulus (anchor portion 28), or vice versa, such that a predetermined one of the band 16 or anchor portion 28 fails in an expected and controlled manner. For example, it is contemplated that one expected mode of failure is that the anchor portion 28 "uncoils" via a permanent, plastic deformation. In such a case, the first modulus (band 16) can be greater than the second modulus (anchor portion 28) such that the band 16 is capable of elastically deforming to a greater extent than the anchor portion 28, such that the anchor portion 28 plastically deforms first (e.g., "uncoils") while the band 16 remains elastic and generally non-deformed. The plastic deformation of the anchor portion 28 can occur relatively slowly and minimize shock forces such that the tissue-engaging portion 26 of the tissue retention member 12 does not damage the retained tissue 29.

The following design example assumes that the material of the band 16 has a durometer value of 60 D (see Table 1). The theoretical maximum load for the silicone stay 10 is about 17 lbs. (e.g., 1520 psi*pi*r^2=17 lbs.), where the minimum diameter of the stay 10 was used (~0.12") to determine the max load before the silicone will fail. Therefore, the coil 40 can be configured to withstand a maximum load of at least 17 lbs. before deflection occurs. Additionally, the coil 40 can also be configured to withstand a minimum load above a desired engineering specification, such as 5 lbs. or the like. The coil's parameters may change (e.g., coil internal diameter, wire diameter, number of coils, etc.) to achieve the similar elongation without deflection. Therefore, the coil 40 is configured to be able to elongate with the material to at least the ultimate elongation for the 60 D (450%) with k=330 psi. Still, if it is desired that the coil 40 fail before the longitudinal body 18, then the coil 40 can be adapted to withstand a maximum load less than the above-described 17 lbs. It is understood that various other values are completed, and the values discussed in this example are subject to change.

In addition or alternatively, the pullout strength of the tissue retention member 12 from the first end 22 can be modified by adjusting the insertion length and/or position of the anchor portion 28 within the first end 22 of the band 16. For example, to increase the pullout strength, the anchor portion 28 can extend a relatively greater distance into the first end 22, such as more than about 5/16" or 1/2". In another example, to increase the pullout strength, the tissue retention member 12 can be positioned inwardly within first end 22 of the band 16 such that more of the tissue-engaging portion 26 is embedded therein. For example, as shown in FIG. 5D, relatively more of the tissue retention member 12 can be positioned within the first end 22 of the band 16 such that the transition region 32 is spaced a greater distance $D_1$ from a face 23 of the first end 22 of the band 16. Thus, a relatively greater amount of the body material (e.g., silicone, urethane, etc.) is located between the transition region 32 and the face 23 of the first end 22 to thereby increase the pullout strength of the tissue retention member 12. The distance $D_1$ between the transition region 32 and the face 23 can be adjusted to provide a desired pullout strength and/or desired failure mode. Additionally, a relatively greater amount of the body material disposed between the transition region 32 and the face 23 of the first end 22 can provide relatively more stability at the interface between the tissue-engaging portion 26 and the first end 22.

Figure 4B:
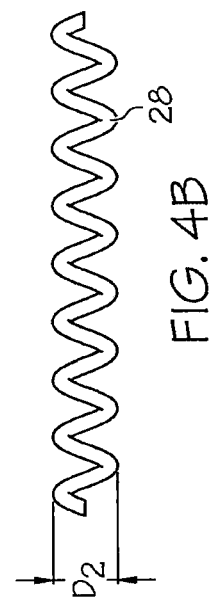
FIG. 4B is a side view of an example anchor portion of the tissue retention member of FIG. 3.

In addition or alternatively, the longitudinal body 18 of the elastomeric band 16 can include a generally uniform cross-sectional dimension with a plurality of the hubs 20 spaced at regular intervals along the length thereof. As shown in FIGS. 5A-5D, the anchor portion 28 can have a cross-sectional dimension less than the cross-sectional dimension of the longitudinal body 18 such that the anchor portion 28 can be at least partially embedded within the first end 22 of the band 16. For example, as shown in FIGS. 4B and 5A, where both of the longitudinal body 18 and coil 40 have a generally circular cross-sectional geometry, the cross-sectional diameter $D_2$ of the coil 40 can be relatively smaller than the cross-sectional diameter $D_3$ of the longitudinal body 18. Additionally, the plurality of hubs 20 can be substantially similar to thereby define a maximum cross-sectional dimension of the surgical stay 10. As shown in FIGS. 1-2, the cross-section dimension $D_4$ of the hubs 20 can be relatively larger than the cross-sectional dimension $D_3$ of the longitudinal body 18 to enable the hubs 20 to engage the retractor frame 60. For example, as shown in FIG. 5C, even though the projections 48 can be embedded within the hubs 20 and may have a relatively larger cross-sectional geometry than the longitudinal body 18, the central member 50 of the anchor portion 28C can still have a cross-sectional dimension less than the cross-sectional dimension of the longitudinal body 18. As a result, all of the longitudinal body 18 (and the hubs 20, 24, if present) are functional and the stay 10 does not include a handle of any kind. For example, each of the hubs 20, 24 can be substantially similar, define a maximum cross-sectional dimension of the surgical stay 10, and/or be spaced at regular intervals along the length of the longitudinal body 18. Similarly, although a cuff, collar, retaining wire, other mechanical fastener, etc. can be used to couple the anchor portion 28 to the first end 22, the cross-sectional diameter $D_3$ of the longitudinal body 18 and/or the cross-section dimension $D_4$ of the hubs 20 is not considered to appreciably increase, and the stay 10 is still considered to not include a handle.

As noted herein, even the hub 24 at the first end 22 of the band 16 is provided with a frame engagement surface 72 and is fully functional for engagement with the frame 60. Thus, because all of the hubs 20, 24 on the band 16 are usable with the frame 60 (and/or surgical instruments), it is understood that the stay 10 does not include a handle of any kind That is, any portion of the stay 10 can be gripped by a user to manipulate the stay 10 as desired and no portion of the stay 10 provides a relatively greater advantage in manipulating the stay 10. Moreover, the handle-less stay does not have the limitations of the conventional stay and allows more of the stay to be used for retraction. When the conventional rigid handle and the surgical frame do interact, the resultant lever action of the handle about the frame can disengage the tissue retention member(s) from the tissue. Through increased stay capacity and flexibility, a handle-less stay does not exhibit such characteristic disengagement. The removal of the stay handle will allow for greater precision during placement of the stay and for placement via surgical instruments, such as hemostats and the like. These enhancements provide an increased margin of safety to the clinician and the patient due to increased visibility, control, and handling during placement. The handle-less stay can also be used with surgical instruments (e.g., hemostats and the like), either together with or in place of a traditional surgical refractor frame, such as during relatively small and/or delicate surgeries (e.g., ear, nose, throat surgeries, etc.).

With additional reference to FIGS. 6-8, the stay 10 is usable with a refractor frame 60 that is adapted to surround all or part of a surgical site 62 and act as a support for the stay 10, or series of stays 10, so that the stay(s) 10 can hold the incision 30 open. Example frames are discussed in U.S. Pat. Nos. 6,090,043 and 5,951,467, the entire disclosures of which are incorporated herein by reference thereto. Still, it is understood that the stay 10 can also be used with surgical instruments (e.g., hemostats and the like), either in place of or together with a traditional surgical retractor frame. In one example, the stay 10 can be used solely with surgical instruments during relatively small and/or delicate surgeries (e.g., ear, nose, throat surgeries, etc.). Accordingly, the frame 60 is only illustrated schematically and described to provide context for the examples described herein. The frame 60 has a flange 64 with an upper surface 66 and a lower surface 68. The upper surface 66 and the lower surface 68 are illustrated as generally planar, though can have other geometries. The frame 60 is provided with notches 70 extending from the upper surface 66 to the lower surface 68. The notches 70 are adapted to releasably receive the body 18 of the band 16. The notch 70 is preferably sized about as large as the body 18 of the band 16, sometimes smaller. Should the notch 70 be sized smaller than the body 18 of the band 16, the frame 60 will slightly compress the body 18 as it is inserted into the notch 70.

The stay 10 is used by placing the tissue engaging portion 26 of the tissue retention member 12 on the tissue 29 to be retained and inserting the body 18 of the band 16 in one of the notches 70 of the frame 60. The stay 10 is prevented from moving forward, or towards the surgical site 62, and from being pulled through the notch 70 by mechanical interference. More specifically, the hub 20 adjacent the frame 60 abuts a portion of the lower surface 68 of the frame 60 surrounding the notch 70 thereby preventing movement of the stay 10 except for stretching of the elastic band 16.

As illustrated in FIG. 7, the example hubs 20 can have an engagement surface 72 that is in contact, such as face-to-face contact, with the lower surface 68 of the frame 60. This engagement provides a distributed area where tension placed on the band 16 will be transferred to the frame 60. This distributed area is larger than, and therefore capable of absorbing greater amounts of tension, compared to a stay without hubs (not shown) or with spherical hubs (not shown), either of which can compress their way through the notch 70.

For example, the illustrated portion 74 of the engagement surface 72 that does contact the lower surface 68 can be in a flat relationship with, and make face-to-face contact with, the lower surface 68. Therefore, the forces placed on the band 16 are distributed over a broad area which is capable of absorbing relatively greater amounts of tension. When greater tension is placed on the band 16, the body 18 of the band 16 will have a tendency to be pulled further into the notch 70 and the hub 20 will have a tendency to be drawn into tighter engagement with the lower surface 68 of the frame 60, resulting in the arrangement shown in FIG. 7.

Moreover, even the hub 24 at the first end 22 of the band 16 is provided with a frame engagement surface 72 and is fully functional for engagement with the frame 60. As shown in FIG. 8, the handle-less design allows for greater precision and flexibility during placement and use of the stay 10. For example, the tissue-engaging portion 26 can be used to retain tissue 29 located extremely near the retractor frame 60. The anchor portion 28 can conform to the retractor frame 60 and to the needs of the surgeon. Still, as previously discussed, the hubs 20, 24 can have various geometries that may or may not provide planar contact with the frame 60.

Referring now to FIGS. 9-18, an alternative example stay 100 is depicted. The use of elastic polymer materials in a stay has been known to cause some issues with functionality. In particular, the elastic polymer materials may interact with more rigid or sharp materials, such as metal retractor frames, which may cause the stays to crack and fail. This can result in operating room hazards for patients and caregivers. Silicone has especially poor tear properties and is often used in surgical stays. Silicon with higher relative durometers accentuates tearing vulnerabilities, but is often preferred clinically for the responsiveness (force/elongation) it provides. Tearing properties are more acute in the context of retractor frames with metal, older age, damage, friction-fitted retention, or homemade retention devices, among other devices. The example stay 100 meets a clinical need for an elastically responsive surgical stay having higher hook retention strength and reliability.

The example stay 100 allows the user to adjust the stay due to its elastic properties to better suit a wider variety of clinical needs without compromising safety. The design provides increased compatibility with a number of retractor frame types and materials, while decreasing the overall risk of failure and possible associated injuries to patients and their physicians. The example stay 100 provides a lower profile with decreased elasticity so that a given force can be applied over a shorter distance of elongation.

Referring again to FIGS. 9-18, the example surgical stay 100 incorporates a central, hollow space 102 that travels the long axis A-A of the stay 100 in regions prone to polymer crack formation and abrasion. The regions which are most prone to cracking and/or abrasion are normally located at the stay and the retention mechanism interface, which is typically a notched retractor frame. The hollow space 102 is provided along at least part of the length L1 of the stay, but, as discussed above in the examples presented in FIGS. 1-8, is not necessary for the stay to function. The hollow interior space 102 is a unique additional feature that yields clinical benefits.

The example stay 100 has an overall length L and a hollow interior space 102. The hollow space 102 extends along part of the length L1 of the stay 100. The remainder of the length L2 of the elongated member is solid and may be used to house a tissue retention member, such as a hook 106. This hollow space 102 improves the surgical stay's tear properties by allowing for material deformation into the hollow space 102 when the stay 100 is positioned in a groove of a retractor frame, shown in FIG. 6. As a result, materials which otherwise are prone to crack-related failure, such as high-durometer silicone, can effectively function in a stay 100. Other elastomers may also be used. By contrast, a stay which does not utilize a hollow space 102 cannot undergo the compression and displacement to alleviate the stress which induces crack formation and propagation. The material bulk of non-hollow stays becomes compressed in an elongated manner, and internal stresses further assist in crack initiation and propagation.

The example stay 100 may be injection molded from a variety of different elastomeric materials and made into a variety of different morphologies. A stay 100 formed by injection molding has many advantages from both design and manufacturing perspectives. For example, parts may be joined together during the molding process so that no voids or openings are present, which provides the ability to autoclave the stays and reuse them.

Figure 9:
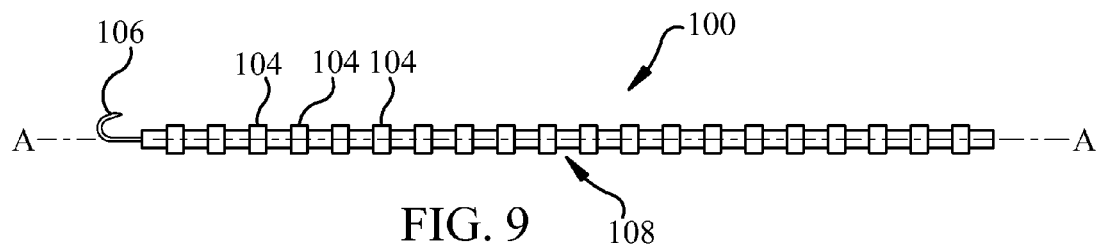
FIG. 9 is a side view of an alternative example surgical stay.
Figure 10:
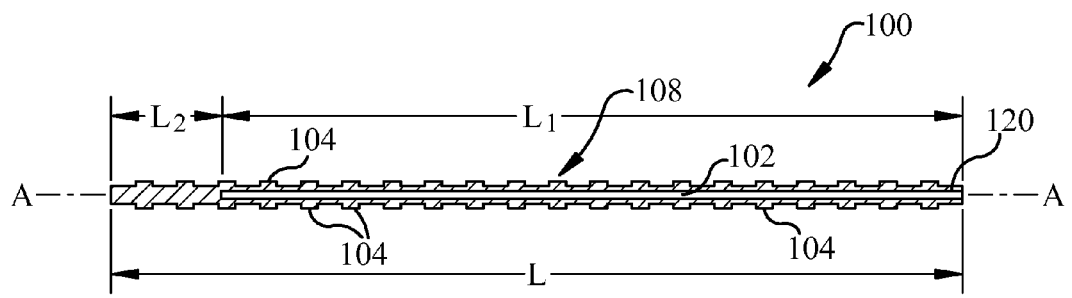
FIG. 10 is a cross-sectional view of the example surgical stay of FIG. 9.
Figure 11:
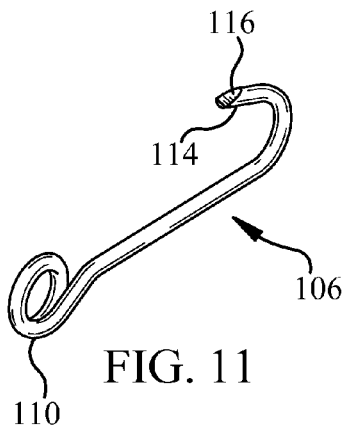
FIG. 11 is a perspective view of a tissue engaging portion for use with the stay of FIG. 9.
Figure 12:
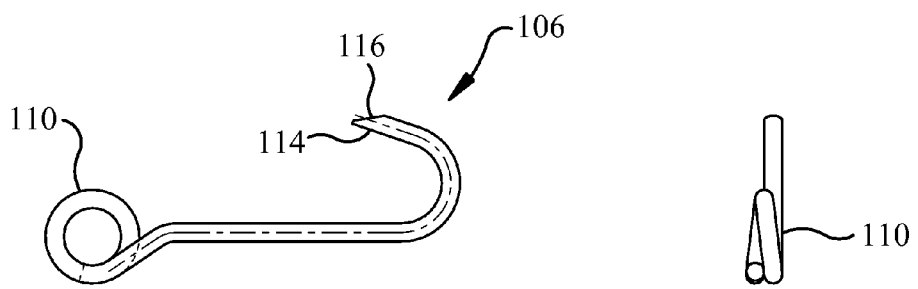
FIG. 12 is a side view of the tissue engaging portion of FIG. 11.
Figure 13:
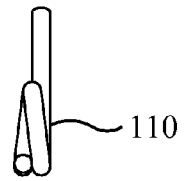
FIG. 13 is an end view of the tissue engaging of FIG. 11.
Figure 15:
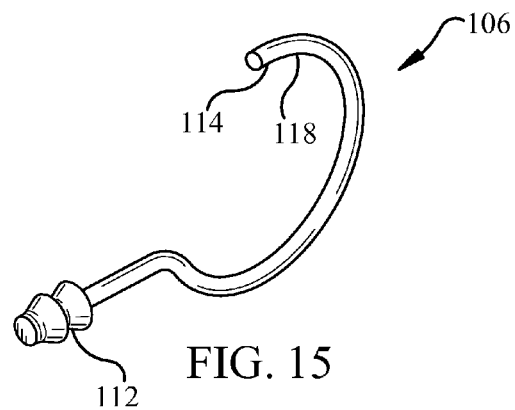
FIG. 15 is a perspective view of an alternative tissue engaging portion for use with the stay of FIG. 9.
Figure 16:
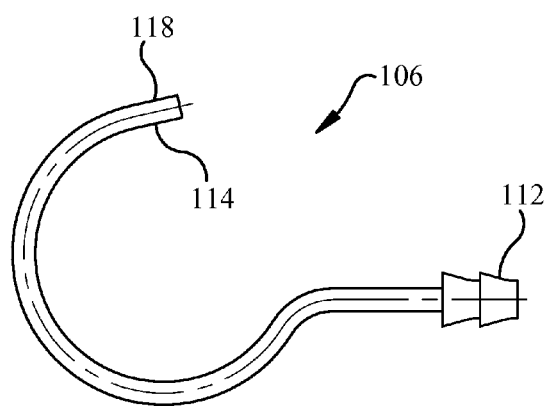
FIG. 16 is a side view of the tissue engaging portion of FIG. 15.
Figure 17:
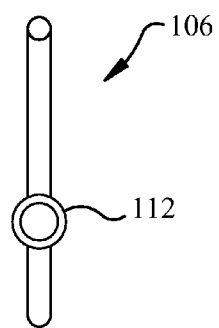
FIG. 17 is an end view of the tissue engaging portion of FIG. 15.
Figure 14:
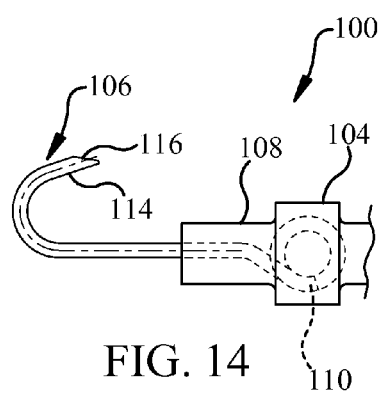
FIG. 14 is a partial side view of the example surgical stay of FIG. 9 incorporating the tissue engaging portion of FIG. 11.
Figure 18:
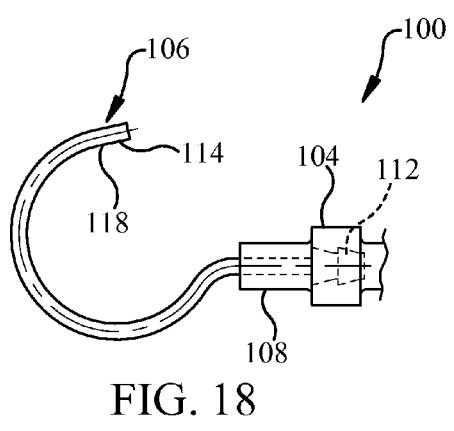
FIG. 18 is a partial side view of the example surgical stay of FIG. 9 incorporating the tissue engaging portion of FIG. 15.

FIGS. 9, 14, and 18 depict an example stay 100 that incorporates a hook 106. Each stay 100 has an elongated body member 108. The elongated body member 108 may be substantially cylindrical and may include hubs 104, as shown. The elongated body member 108 may alternatively have other shapes. The hubs 104 may also be substantially cylindrical in shape, or may be other shapes, if desired. The elongated member 108 is shown as including the hollow inner portion 102 along a significant portion of its length, meaning at least half its length. In some embodiments, the hollow inner portion 102 may be along most of the length of the elongated member 108. An anchor end 110, 112 of each hook 106 is over-molded with the material of the stay 100, as shown best in the details of FIGS. 14 and 18.

In the example shown in FIG. 9, the hollow portion 102 extends substantially along the length L of the stay 100 and ends near the stay-hook coupling. Other lengths for the hollow portion 102 may be utilized. For example, the hollow portion 102 may take up less of the length of the stay, such as ¾, ½, or some other portion of the length of the stay 100. The hollow portion 102 may be continuous or discontinuous and can have any desired geometry, such as circular, rectangular, triangular, or other shapes. The tip 120 of the hollow portion 102 may be blunt, rounded, pointed, or another geometry. In addition, the stay 100 is shown as having hubs 104. The hubs 104 are optional.

Referring to FIGS. 14 and 18, the detail drawings show the hooks 106 over-molded onto the elongated member 108. Each hook 106 has a tissue retention member or portion 114 and the anchor member 110, 112 is molded into one of the hubs 104 of the elongated member 108. Other designs for the connection between the elongated member 100 and the anchor portions 110, 112 of the hooks 106 may be utilized. For example, the anchors 110, 112 do not need to be positioned in the hubs 104. The anchors 110, 112 could alternatively be projections, barbs, bent portions, bulbs, or have another geometry with retensive properties.

FIGS. 11-14 depict a first example tissue retention member 114 that includes a sharp hook 116, such as a 5 mm sharp hook. In the example shown in FIGS. 11-14, the anchor portion is a coiled end loop 110. The coiled end loop 110 is for coupling with the elongated member 108 of the stay 100, as shown in FIGS. 9 and 14. FIGS. 15-18 depict a second example tissue retention member 114 that has a blunt hook 118 and an anchor portion 112 that has a projection with a multi-tapered barb for coupling with the elongated member 118, as shown in FIG. 18.

Other types of anchors 110, 112 may be utilized, including any of those discussed above with the embodiments of FIGS. 1-8, or as known by those of skill in the art. Other types of tissue engaging portions 114 may also be used, including single hooks, double hooks, clips, rakes, or the like, the invention not being limited to a particular type of tissue engaging portion. Any length L may be provided for the elongated member 108. It is preferred that the surgical stay 100 be injection molded and that no voids be present between the connection of the tissue retention member or hook 106 and the elongated member 108 such that the two parts are integral with one another upon molding.

A first example surgical stay includes an elastomeric elongated member and a tissue retention member. The elastomeric elongated member has a first closed end and a second end, with a substantial portion of the length of the elongated member being hollow. The tissue retention member is coupled to the first end of the elastomeric elongated member such that the tissue retention member extends outwardly from the closed first end. The elongated member and the tissue retention member are integrally joined so that no openings are present therebetween. The surgical stay may be formed by injection molding of the elongated member with the tissue retention member. The tissue retention member may include an anchor portion and a tissue engaging portion, with the anchor portion being positioned inside the elongated member, and the tissue engaging portion extending from the closed first end of the elongated member. The elastomeric elongated member may be made of silicone.

The tissue engaging portion may have at least one hook. The hook may be a sharp hook, a blunt hook, or a clip. The anchor portion may be a coiled portion, a projection, a bulb, a barb, a bent element, or a combination thereof. The hollow portion of the elongated member may extend along at least one-half of the length of the elongated member and may have a substantially cylindrical shape. The elongated member may include a plurality of hubs positioned at spaced locations along at least part of the length of the elongated member. The tissue retention member may include an anchor portion and a tissue engaging portion, and the anchor portion may be positioned at least in part inside one of the hubs of the elongated member. The elongated member may have a substantially cylindrical shape.

Another example surgical stay includes an elongated member having a hollow portion along at least a portion of its length and a tissue retention member. The tissue retention member is integrally coupled to one end of the elongated member via injection molding to provide a void-free connection between the tissue retention member and the elongated member. The tissue retention member may include an anchor portion and a tissue engaging portion, with the anchor portion being positioned inside the elongated member, and the tissue engaging portion extending from at least one end of the elongated member. The elongated member may be made of an elastomeric material, such as silicone, among other materials.

The tissue retention member may have at least one hook and the hook may be at least one of a sharp hook and a blunt hook. The anchor portion may be one or more of a coiled portion, a projection, a bulb, a barb, or a bent element. The hollow portion may extend along at least one-half of the length of the elongated member. The hollow portion may have a substantially tubular, cylindrical shape. The elongated member may include a plurality of hubs positioned at spaced locations along at least part of the length of the elongated member. The tissue retention member may include an anchor portion and a tissue engaging portion, and the anchor portion may be positioned inside at least one of the hubs of the elongated member. The elongated member may be substantially cylindrical.

The above designs allow for a single, universal mechanism of attachment of a functional element which interacts with biological tissue (e.g., hooks, rakes, clamps, etc. of various morphologies and purposes) to an elastic stay body. This single mechanism of attachment simplifies the manufacturing process for creating and supporting various stay types and lowers manufacturing costs. The increased number of stay types will allow for application of this new self-retaining retractor technology to an increased number of surgical procedures heretofore performed without the aid of such technology.

Various beneficial advantages are provided by the surgical stays 10, 100 described herein. The discussion herein describes only some of the many advantages and is not intended to limit the examples described herein. For example, the surgical stays 10, 100 provide a universal mechanism of attachment for various tissue retention systems, while also decreasing manufacturing costs, increasing manufacturing simplicity, and increasing reliability. The stays 10, 100 provide a cost-effective method to expand the breadth of stay tissue retention systems for unique surgical applications. The surgical stays 10, 100 provide increased safety for the operating room staff and surgical patient, decreased tissue damage, increased surgical site visualization, and increased operating room performance. The stays 10, 100 also can provide for control over differing failure modes. The stays 10, 100 reduce the resultant tissue trauma and visual obstruction caused by a rigid stay handle, which is conventional in the industry.

While the above described stay is discussed in the context of injection molding, other techniques can also be used to form the stay. For example, overmolding or bonding may be used.

The term "substantially," as used herein, is a term of estimation. The term "substantial," as used herein, is a term of magnitude.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. A surgical stay comprising:
    an elastomeric elongated member having a first end and a second end, wherein a portion of a length of the elongated member comprising the first end comprises a solid cross-section and another portion of the length of the elongated member comprises a hollow cross-section; and
    a tissue retention member coupled to and directly contacting the first end of the elastomeric elongated member, the tissue retention member comprising an anchor portion and a tissue engaging portion, wherein the anchor portion connects directly into the first end such that the anchor portion extends into and is secured within the solid cross-section of the elastomeric elongated member, and wherein the tissue engaging portion extends outwardly from the first end.

2. The surgical stay of claim 1, wherein the elongated member includes a plurality of hubs positioned at spaced locations along at least part of the length of the elongated member.

3. The surgical stay of claim 2, wherein the anchor portion is positioned at least in part inside one of the hubs of the elongated member.

4. The surgical stay of claim 1, wherein the surgical stay is formed by injection molding of the elongated member with the tissue retention member.

5. The surgical stay of claim 1, wherein the elastomeric elongated member is made of silicone.

6. The surgical stay of claim 1, wherein the tissue engaging portion has at least one hook, the hook is at least one of a sharp hook and a blunt hook, and the anchor portion is at least one of a coiled portion, a loop, a projection, a bulb, a barb, and a bent element.

7. The surgical stay of claim 1, wherein the other portion of the length of the elongated member comprising the hollow cross-section extends along at least one-half of the length of the elongated member and has a substantially cylindrical shape.

8. The surgical stay of claim 1, wherein the elongated member has a substantially cylindrical shape.

9. A surgical stay comprising:
    an elongated member having a hollow portion along at least a portion of its length and a solid portion along at least another portion of its length, wherein the elongated member includes a plurality of integral hubs positioned at spaced locations along at least part of its length; and
    a tissue retention member coupled directly in to one end of said elongated member, wherein the tissue retention member includes an anchor portion and a tissue engaging portion, the anchor portion extends directly into the solid portion of the elongated member and is positioned inside at least one of the plurality of hubs, and the tissue engaging portion extends from the one end of the elongated member, and
    wherein the surgical stay is formed by injection molding of the elongated member with the tissue retention member.

10. The surgical stay of claim 9, wherein the elongated member is made of an elastomeric material.

11. The surgical stay of claim 9, wherein the elongated member is made of silicone.

12. The surgical stay of claim 9, wherein the tissue retention member has at least one hook and the hook is at least one of a sharp hook and a blunt hook.

13. The surgical stay of claim 9, wherein the anchor portion is at least one of a coiled portion, a loop, a projection, a bulb, a barb, and a bent element.

14. The surgical stay of claim 9, wherein the hollow portion extends along at least one-half of the length of the elongated member.

15. The surgical stay of claim 9, wherein the hollow portion has a substantially tubular, cylindrical shape.

16. The surgical stay of claim 9, wherein the elongated member is substantially cylindrical.

17. The surgical stay of claim 9, wherein the anchor portion extends into more than one of the plurality of hubs.

18. A surgical stay comprising:
   an elastomeric elongated member having a first end and a second end, wherein a portion of a length of the elongated member comprising the first end comprises a solid cross-section and another portion of the length of the elongated member comprises a hollow cross-section, wherein the elastomeric elongated member includes a plurality of integral hubs positioned at spaced locations along at least part of the length of the elastomeric elongated member; and
   a tissue retention member directly integrated into the first end of the elastomeric elongated member, the tissue retention member comprising an anchor portion and a tissue engaging portion, wherein the anchor portion connects directly into the first end such that the anchor portion extends into and is secured within the solid cross-section and at least one of the plurality of hubs, and wherein the tissue engaging portion extends outwardly from the first end.

19. The surgical stay of claim 18, wherein the tissue engaging portion has at least one hook, the hook is at least one of a sharp hook and a blunt hook, and the anchor portion is at least one of a coiled portion, a loop, a projection, a bulb, a barb, and a bent element.

20. The surgical stay of claim 18, wherein the anchor portion extends into more than one of the plurality of hubs.

* * * * *